(12) United States Patent
Kovacs et al.

(10) Patent No.: US 11,311,301 B2
(45) Date of Patent: Apr. 26, 2022

(54) FLEXIBLE BONE REAMER

(71) Applicant: Biomet Manufacturing, LLC, Warsaw, IN (US)

(72) Inventors: Michael Francis Kovacs, Warsaw, IN (US); Thomas M. Vanasse, Gainesville, FL (US)

(73) Assignee: Biomet Manufacturing, LLC, Warsaw, IN (US)

(*) Notice: Subject to any disclaimer, the term of this patent is extended or adjusted under 35 U.S.C. 154(b) by 254 days.

(21) Appl. No.: 16/749,684

(22) Filed: Jan. 22, 2020

(65) Prior Publication Data

US 2020/0155170 A1  May 21, 2020

Related U.S. Application Data

(63) Continuation of application No. 14/460,079, filed on Aug. 14, 2014, now abandoned.

(51) Int. Cl.
*A61B 17/16* (2006.01)
*A61B 17/17* (2006.01)

(52) U.S. Cl.
CPC ...... *A61B 17/1631* (2013.01); *A61B 17/1615* (2013.01); *A61B 17/1684* (2013.01); *A61B 17/1778* (2016.11); *A61B 2017/1602* (2013.01)

(58) Field of Classification Search
CPC ............ A61B 17/1615; A61B 17/1631; A61B 17/1684; A61B 17/1664; A61B 17/1666; A61B 17/1675
See application file for complete search history.

(56) References Cited

U.S. PATENT DOCUMENTS

| | | | |
|---|---|---|---|
| 1,923,177 A | 8/1933 | Tucker | |
| 3,412,733 A | 11/1968 | Ross | |
| 3,630,204 A | 12/1971 | Fishbein | |
| 3,633,583 A | 1/1972 | Fishbein | |
| 3,702,611 A | 11/1972 | Fishbein | |
| 4,011,025 A | 3/1977 | Kress | |
| 4,023,572 A | 5/1977 | Weigand et al. | |
| 4,116,200 A | 9/1978 | Braun et al. | |
| 4,131,116 A | 12/1978 | Hedrick | |
| 4,199,284 A | 4/1980 | Kress et al. | |

(Continued)

FOREIGN PATENT DOCUMENTS

| | | |
|---|---|---|
| AU | 2014249415 A1 | 10/2015 |
| CA | 3030139 A1 | 1/2018 |

(Continued)

OTHER PUBLICATIONS

"U.S. Appl. No. 13/324,188, Final Office Action dated Sep. 4, 2014", 11 pgs.

(Continued)

*Primary Examiner* — Samuel S Hanna

(74) *Attorney, Agent, or Firm* — Schwegman Lundberg & Woessner, P.A.

(57) ABSTRACT

A bone reamer is provided and may include a shaft and a cutting element. The shaft may include a proximal end, a distal end, and a flexible portion. The flexible portion may be disposed between the proximal and distal ends. The cutting element may be carried by the shaft and may include a cutting surface facing the distal end of the shaft. The distal end of the shaft may be offset from the cutting surface.

17 Claims, 6 Drawing Sheets

(56) References Cited

U.S. PATENT DOCUMENTS

| | | |
|---|---|---|
| 4,239,427 A | 12/1980 | Walton, II |
| 4,504,165 A | 3/1985 | Moeremans |
| 4,565,345 A | 1/1986 | Templeman |
| 4,614,457 A | 9/1986 | Sammon |
| 4,621,637 A | 11/1986 | Fishbein |
| 4,672,964 A | 6/1987 | Dee et al. |
| 4,768,405 A | 9/1988 | Nickipuck |
| 4,811,632 A | 3/1989 | Salyer |
| 5,030,219 A | 7/1991 | Matsen, III et al. |
| 5,032,132 A | 7/1991 | Matsen, III et al. |
| 5,055,106 A | 10/1991 | Lundgren |
| 5,092,719 A | 3/1992 | Zsiger |
| 5,100,267 A | 3/1992 | Salyer |
| 5,116,165 A | 5/1992 | Salyer |
| 5,171,312 A | 12/1992 | Salyer |
| 5,171,313 A | 12/1992 | Salyer |
| 5,203,653 A | 4/1993 | Kudla |
| 5,236,289 A | 8/1993 | Salyer |
| 5,236,433 A | 8/1993 | Salyer |
| 5,282,804 A | 2/1994 | Salyer |
| 5,295,992 A | 3/1994 | Cameron |
| 5,299,893 A | 4/1994 | Salyer et al. |
| 5,376,092 A | 12/1994 | Hein et al. |
| 5,462,548 A | 10/1995 | Pappas et al. |
| 5,489,310 A | 2/1996 | Mikhail |
| 5,499,986 A | 3/1996 | Dimarco |
| 5,501,686 A | 3/1996 | Salyer |
| 5,562,702 A | 10/1996 | Huitema et al. |
| 5,624,447 A | 4/1997 | Myers |
| 5,658,290 A | 8/1997 | Lechot |
| 5,709,688 A | 1/1998 | Salyer |
| 5,741,266 A | 4/1998 | Moran et al. |
| 5,746,548 A | 5/1998 | Crandall |
| 5,755,719 A | 5/1998 | Frieze et al. |
| 5,800,551 A | 9/1998 | Williamson et al. |
| 5,817,096 A | 10/1998 | Salyer |
| 5,824,181 A | 10/1998 | Salyer et al. |
| 5,897,558 A | 4/1999 | Frieze et al. |
| 5,908,423 A | 6/1999 | Kashuba et al. |
| 5,947,805 A | 9/1999 | Van Osenbruggen |
| 5,976,148 A | 11/1999 | Charpenet et al. |
| 5,980,170 A | 11/1999 | Salyer |
| 6,001,105 A | 12/1999 | Salyer |
| 6,045,302 A | 4/2000 | Orr |
| 6,053,922 A | 4/2000 | Krause et al. |
| 6,102,915 A | 8/2000 | Bresler et al. |
| 6,132,469 A | 10/2000 | Schroeder |
| 6,168,600 B1 | 1/2001 | Grace et al. |
| 6,221,076 B1 | 4/2001 | Albrektsson et al. |
| 6,245,074 B1 | 6/2001 | Allard et al. |
| 6,250,858 B1 | 6/2001 | Salyer |
| 6,283,972 B1 | 9/2001 | Riley |
| 6,312,325 B1 | 11/2001 | Van Osenbruggen |
| 6,409,732 B1 | 6/2002 | Salyer |
| 6,416,553 B1 | 7/2002 | White et al. |
| 6,428,543 B1 | 8/2002 | Salyer |
| 6,458,161 B1 | 10/2002 | Gibbs et al. |
| 6,884,246 B1 | 4/2005 | Sonnabend et al. |
| 6,889,582 B2 | 5/2005 | Wilhelm |
| 7,097,646 B2 | 8/2006 | Schantz |
| 7,220,264 B1 | 5/2007 | Hershberger |
| 7,320,555 B2 | 1/2008 | Chang et al. |
| 7,479,144 B2 | 1/2009 | Myers |
| 7,503,921 B2 | 3/2009 | Berthusen et al. |
| 7,574,768 B2 | 8/2009 | Morris et al. |
| 7,608,076 B2 | 10/2009 | Ezzedine |
| 7,632,276 B2 | 12/2009 | Fishbein |
| 7,670,343 B2 | 3/2010 | Meridew et al. |
| 7,722,615 B2 | 5/2010 | Botimer |
| 8,123,753 B2 | 2/2012 | Poncet |
| 8,197,487 B2 | 6/2012 | Poncet et al. |
| 8,366,713 B2 | 2/2013 | Long |
| 2002/0095214 A1 | 7/2002 | Hyde, Jr. |
| 2002/0099380 A1 | 7/2002 | Salyer et al. |
| 2002/0111689 A1 | 8/2002 | Edward, Jr. et al. |
| 2003/0135219 A1 | 7/2003 | Salyer et al. |
| 2003/0163135 A1 | 8/2003 | Hathaway |
| 2003/0212402 A1 | 11/2003 | White et al. |
| 2003/0220646 A1 | 11/2003 | Thelen et al. |
| 2003/0220647 A1 | 11/2003 | Mccallum et al. |
| 2004/0097947 A1 | 5/2004 | Wolford et al. |
| 2005/0113836 A1 | 5/2005 | Lozier et al. |
| 2005/0216020 A1 | 9/2005 | Orton |
| 2006/0129157 A1 | 6/2006 | Desarzens et al. |
| 2006/0217730 A1 | 9/2006 | Termanini |
| 2006/0241629 A1 | 10/2006 | Krebs et al. |
| 2006/0277811 A1 | 12/2006 | Peterson |
| 2007/0038302 A1 | 2/2007 | Shultz et al. |
| 2007/0225723 A1 | 9/2007 | Berthusen |
| 2009/0138016 A1 | 5/2009 | Berthusen et al. |
| 2009/0173191 A1 | 7/2009 | Davidson et al. |
| 2010/0063507 A1 | 3/2010 | Sidebotham et al. |
| 2010/0069907 A1 | 3/2010 | Sidebotham et al. |
| 2010/0161060 A1 | 6/2010 | Schaller et al. |
| 2011/0213371 A1 | 9/2011 | Anthony et al. |
| 2012/0239042 A1 | 9/2012 | Lappin et al. |
| 2013/0138109 A1 | 5/2013 | Long et al. |
| 2013/0150858 A1* | 6/2013 | Primiano ............ A61B 17/1675 606/80 |
| 2013/0150859 A1 | 6/2013 | Kehres et al. |
| 2015/0265288 A1 | 9/2015 | Guederian |
| 2015/0342620 A1 | 12/2015 | Winslow |
| 2016/0045207 A1 | 2/2016 | Kovacs et al. |
| 2017/0035442 A1 | 2/2017 | Smith et al. |
| 2018/0008293 A1 | 1/2018 | Kovacs et al. |
| 2018/0303618 A1 | 10/2018 | Kovacs et al. |

FOREIGN PATENT DOCUMENTS

| | | |
|---|---|---|
| CN | 1193899 A | 9/1998 |
| CN | 198461 | 6/2007 |
| CN | 106687054 A | 5/2017 |
| DE | 202009007979 U1 | 8/2009 |
| EP | 0139356 A1 | 5/1985 |
| EP | 1550419 B1 | 2/2007 |
| EP | 2586387 A1 | 5/2013 |
| EP | 2706931 A1 | 3/2014 |
| JP | 2005501648 A | 1/2005 |
| JP | 2017523875 A | 8/2017 |
| WO | WO-03022162 A1 | 3/2003 |
| WO | WO-2008040433 A1 | 4/2008 |
| WO | WO-2013152102 A1 | 10/2013 |
| WO | WO-2014164346 A1 | 10/2014 |
| WO | WO-2016025712 A2 | 2/2016 |

OTHER PUBLICATIONS

"U.S. Appl. No. 13/324,188, Non Final Office Action dated Apr. 29, 2014", 11 pgs.

"U.S. Appl. No. 14/460,079, Advisory Action dated Jan. 3, 2020", 5 pgs.

"U.S. Appl. No. 14/460,079, Advisory Action dated Sep. 1, 2017", 3 pgs.

"U.S. Appl. No. 14/460,079, Advisory Action dated Oct. 15, 2018", 3 pgs.

"U.S. Appl. No. 14/460,079, Examiner Interview Summary dated Oct. 28, 2019", 3 pgs.

"U.S. Appl. No. 14/460,079, Final Office Action dated Jun. 23, 2017", 12 pgs.

"U.S. Appl. No. 14/460,079, Final Office Action dated Jul. 19, 2018", 21 pgs.

"U.S. Appl. No. 14/460,079, Final Office Action dated Oct. 22, 2019", 17 pgs.

"U.S. Appl. No. 14/460,079, Non Final Office Action dated Feb. 8, 2018", 19 pgs.

"U.S. Appl. No. 14/460,079, Non Final Office Action dated Mar. 23, 2017", 8 pgs.

"U.S. Appl. No. 14/460,079, Non Final Office Action dated Jun. 20, 2019", 17 pgs.

"U.S. Appl. No. 14/460,079, Notice of Non-Compliant Amendment dated Mar. 25, 2019", 3 pgs.

(56) References Cited

OTHER PUBLICATIONS

"U.S. Appl. No. 14/460,079, Response filed May 8, 2018 to Non Final Office Action dated Feb. 8, 2018", 11 pgs.
"U.S. Appl. No. 14/460,079, Response filed May 16, 2017 to Non Final Office Action dated Mar. 23, 2017", 10 pgs.
"U.S. Appl. No. 14/460,079, Response filed May 22, 2019 to Notice of Non-Compliant Amendment dated Mar. 25, 2019", 6 pgs.
"U.S. Appl. No. 14/460,079, Response filed Aug. 23, 2017 to Final Office Action dated Jun. 23, 2017", 13 pgs.
"U.S. Appl. No. 14/460,079, Response filed Sep. 20, 2019 to Non-Final Office Action dated Jun. 20, 2019", 13 pgs.
"U.S. Appl. No. 14/460,079, Response filed Oct. 4, 2018 to Final Office Action dated Jul. 19, 2018", 13 pgs.
"U.S. Appl. No. 14/460,079, Response filed Dec. 20, 2019 to Final Office Action dated Oct. 22, 2019", 13 pgs.
"U.S. Appl. No. 14/460,079, Restriction Requirement dated Dec. 27, 2016", 8 pgs.
"U.S. Appl. No. 14/460,079, Response filed Feb. 2, 2017 to Restriction Requirement dated Dec. 27, 2016", 6 pgs.
"Australian Application Serial No. 2015301641, First Examination Report dated Apr. 5, 2019", 3 pgs.
"Australian Application Serial No. 2015301641, Response filed Apr. 30, 2019 to First Examination Report dated Apr. 5, 2019", 13 pgs.
"Australian Application Serial No. 2015301641, Subsequent Examiners Report dated Jun. 6, 2019", 7 pgs.
"Australian Application Serial No. 2015301641, Subsequent Examiners Report dated Oct. 28, 2019", 2 pgs.
"Chinese Application Serial No. 201580048496.2, Office Action dated Jul. 9, 2019", (W/ English Translation), 13 pgs.
"Chinese Application Serial No. 201580048496.2, Office Action dated Nov. 2, 2018", W/ English Translation, 14 pgs.
"Chinese Application Serial No. 201580048496.2, Response filed Mar. 6, 2019 to Office Action dated Nov. 20, 2018", w/ English claims, 8 pgs.
"Chinese Application Serial No. 201580048496.2, Response filed Sep. 18, 2019 to Office Action dated Jul. 9, 2019", w/ English claims, 8 pgs.
"Delta Medial Offset Total Shoulder (Product Rationale-Surgical Technique)", DePuy Orthopaedics, Inc., (2001), 19 pgs.
"Delta Reverse Shoulder System (Surgical Technique)", DePuy Orthopaedics, Inc., (2009), 29 pgs.
"European Serial No. 15754093.1. Response filed Oct. 3, 2017 to Office Action dated Mar. 27, 2017.", 17pgs.
"Global Advantage Shoulder Arthroplasty System", DePuy Inc. Brochure: Design Rationale, (2000), 8 pgs.
"Global Total Shoulder Arthroplasty System", DePuy Orthopaedics, Inc., (1994), 3 pgs.
"International Application Serial No. PCT/US2015/045054, International Preliminary Report on Patentability dated Feb. 23, 2017", 10 pgs.
"International Application Serial No. PCT/US2015/045054, International Search Report dated Feb. 22, 2016", 8 pgs.
"International Application Serial No. PCT/US2015/045054, Invitation to Pay Add'l Fees and Partial Search Rpt dated Dec. 14, 2015", 7 pgs.
"International Application Serial No. PCT/US2015/045054, Written Opinion dated Feb. 22, 2016", 8 pgs.
"Japanese Application Serial No. 2017-508081, Notification of Reasons for Rejection dated Jun. 4, 2019", (W/ English Translation), 8 pgs.
"Reverse Shoulder Prosthesis", Encore Surgical, (2004), 2 pgs.
Matsen, III, Frederick A, et al., "Global Advantage Shoulder Arthroplasty System: Anatomic Shoulder Arthroplasty", DePuy, Surgical Technique, (2000), 32 pgs.
U.S. Appl. No. 14/460,079, filed Aug. 14, 2014, Flexible Bone Reamer.
"Canadian Application Serial No. 2,957,564, Office Action dated Feb. 12, 2020", 4 pages.

* cited by examiner

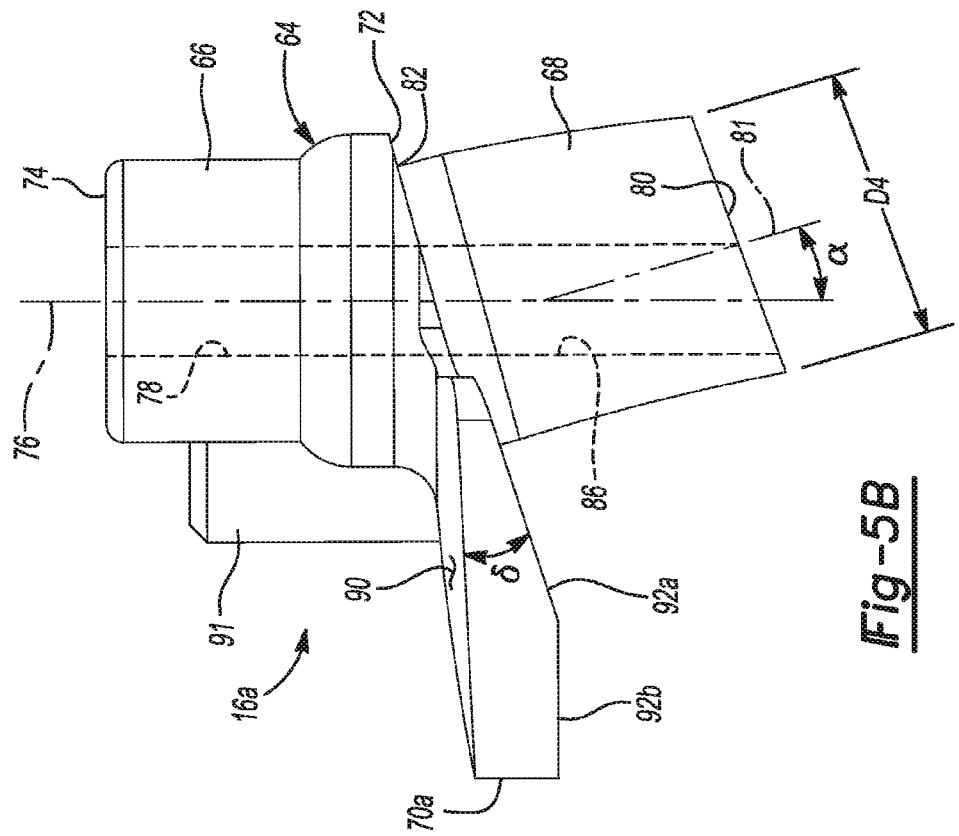
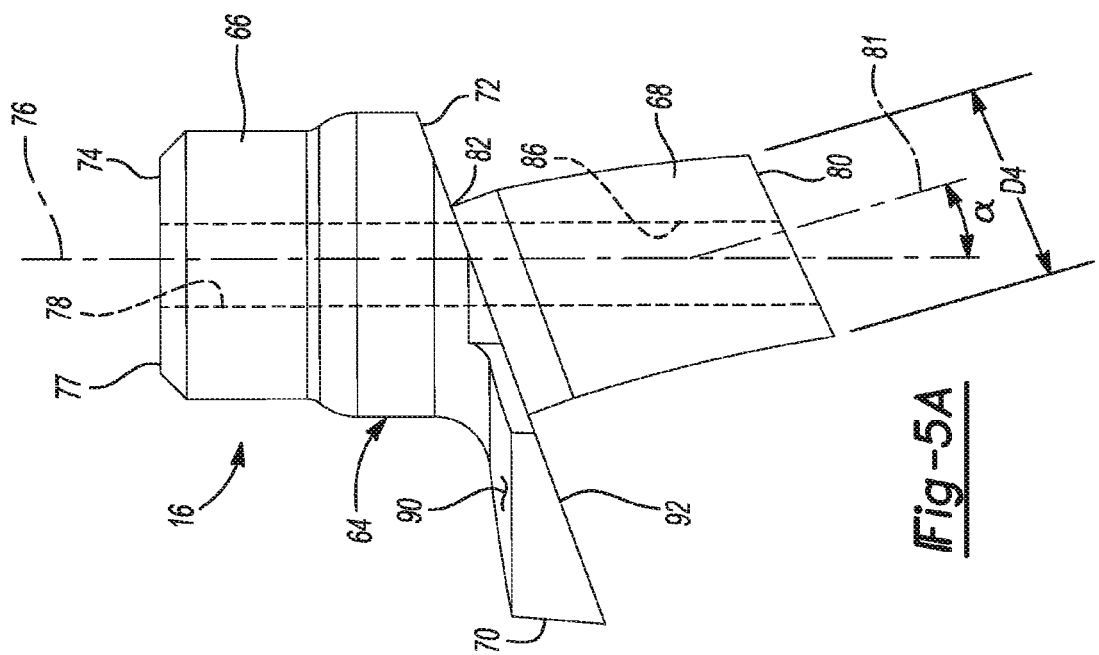

FLEXIBLE BONE REAMER

FIELD

The present disclosure relates generally to a device and method for reaming bone, and more particularly to a bone reamer having a flexible shaft portion.

BACKGROUND

This section provides background information related to the present disclosure and is not necessarily prior art.

Surgical procedures for repairing or reconstructing a joint may require securely fastening a surgical implant to a bone. For example, procedures such as reverse shoulder arthroplasty, for reconstructing a shoulder joint, may require fixing a glenoid implant to a scapula to reproduce or replicate a glenoid cavity on the scapula. These procedures may involve fixing a bone graft to the glenoid and/or reaming the glenoid in order to account for bone deficiencies and erosion of the glenoid over time.

While known surgical procedures for reaming bones, including glenohumeral joints, have proven to be acceptable for their intended purposes, a continuous need for improvement in the relevant arts remains.

SUMMARY

This section provides a general summary of the disclosure, and is not a comprehensive disclosure of its hull scope or all of its features According to one particular aspect; the present disclosure provides a bone reamer. The bone reamer may include a shaft and a cutting element. The shaft may include a proximal end, a distal end, and a flexible portion. The flexible portion may be disposed between the proximal and distal ends. The cutting element may be carried by the shaft and may include a cutting surface facing the distal end of the shaft. The distal end of the shaft may be offset from the cutting surface.

In some configurations, the cutting element may include a plurality of radially extending cutting arms.

In some configurations, the cutting element may include a propeller-shaped profile.

In some configurations, the cutting element may include circular profile.

In some configurations, the shaft may define a cannula.

In some configurations, the cannula may include a first portion having a first diameter and a second portion having a second diameter greater than the first diameter.

In some configurations; at least a portion of the second portion may be aligned with the flexible portion of the shaft.

In some configurations, the shaft may include a plurality of link members selectively coupled to one another to cooperatively define a cannula.

In some configurations, the shaft may further include a ring member coupled to a distal most link member of the plurality of link members. The ring member may define the distal end of the shaft.

In some configurations, the cutting element may be coupled to the ring member.

In some configurations, the cutting element may be monolithically formed with the shaft.

According to another particular aspect, the present disclosure provides a bone reaming system. The bone reaming system may include a bone reamer and a guide. The bone reamer may include a shaft and a cutting element. The cutting element may be carried by the shaft. The shaft may include a proximal end, a distal end, and a flexible portion. The flexible portion may be disposed between the proximal and distal ends. The guide may include a body portion having a boss, a hub and a cannula. The boss may extend along a first longitudinal axis. The hub may extend along a second longitudinal axis. The cannula may be formed within the boss and the hub and may extend along the first longitudinal axis. The second longitudinal axis may form an angle $\alpha$ with the first longitudinal axis.

According to yet another particular aspect, the present disclosure provides a method of reaming a bone. The method may include providing a reaming guide having a first portion extending along a first longitudinal axis and a second portion extending along a second longitudinal axis. The second longitudinal axis may define a non-parallel angle with the first longitudinal axis. The method may also include anchoring the first portion of the reaming guide to the bone. The method may further include coupling a reamer to the second portion of the reaming guide. The reamer may include a shaft and a cutting element carried by the shaft. The method may also include bending the shaft portion. The method may also include rotating the reamer about the hub portion.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5A is a side view of a guide of the reaming systems of FIGS. 1 and 3;

FIG. 5B is a side view of another configuration of the guide of the reaming systems of FIGS. 1 and 3;

Corresponding reference numerals indicate corresponding parts throughout the several views of the drawings.

DETAILED DESCRIPTION

Example embodiments will now be described more fully with reference to the accompanying drawings.

Figure 1:
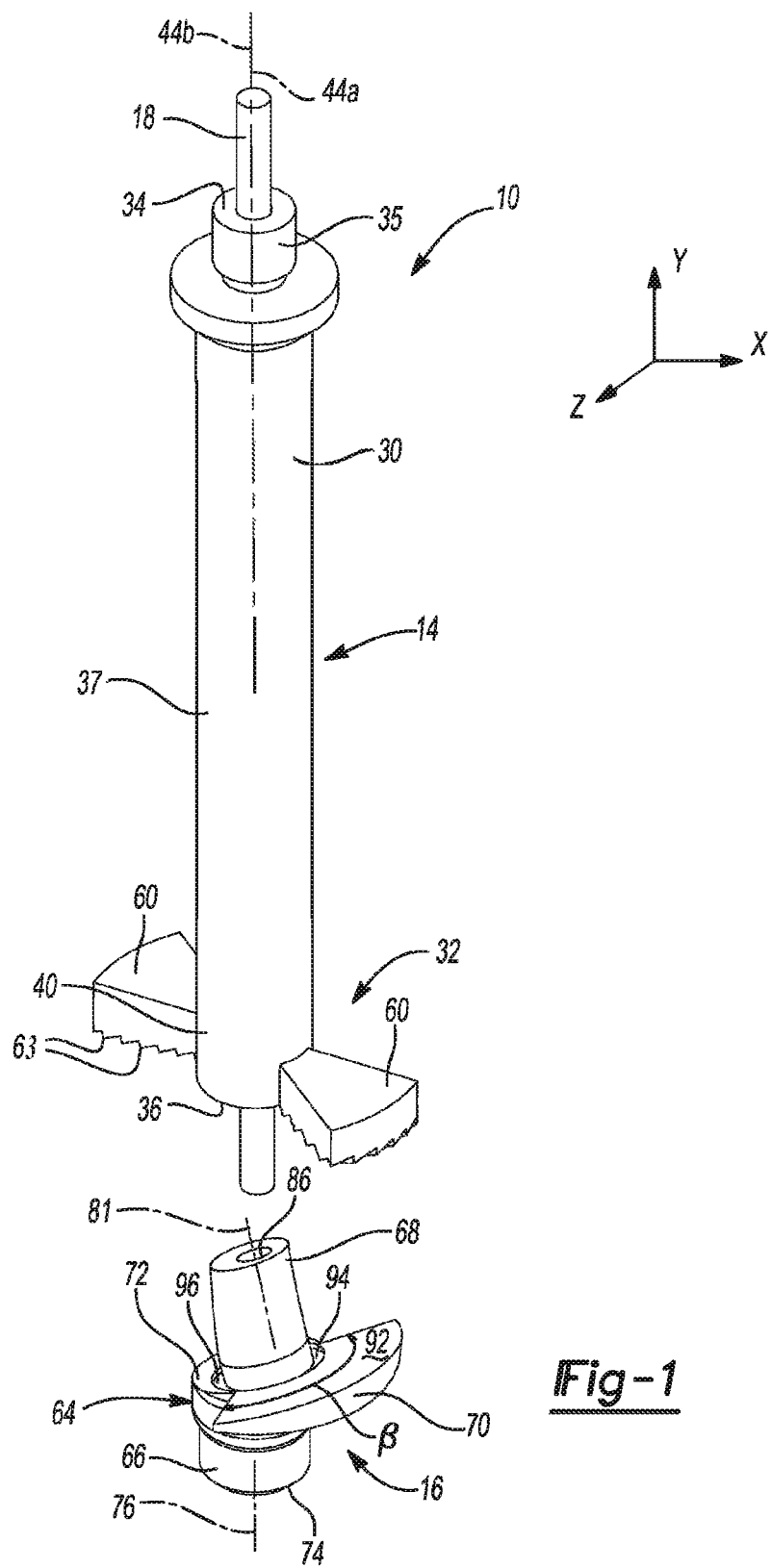
FIG. 1 is perspective view of a reaming system constructed in accordance with the principles of the present disclosure.
Figure 2:
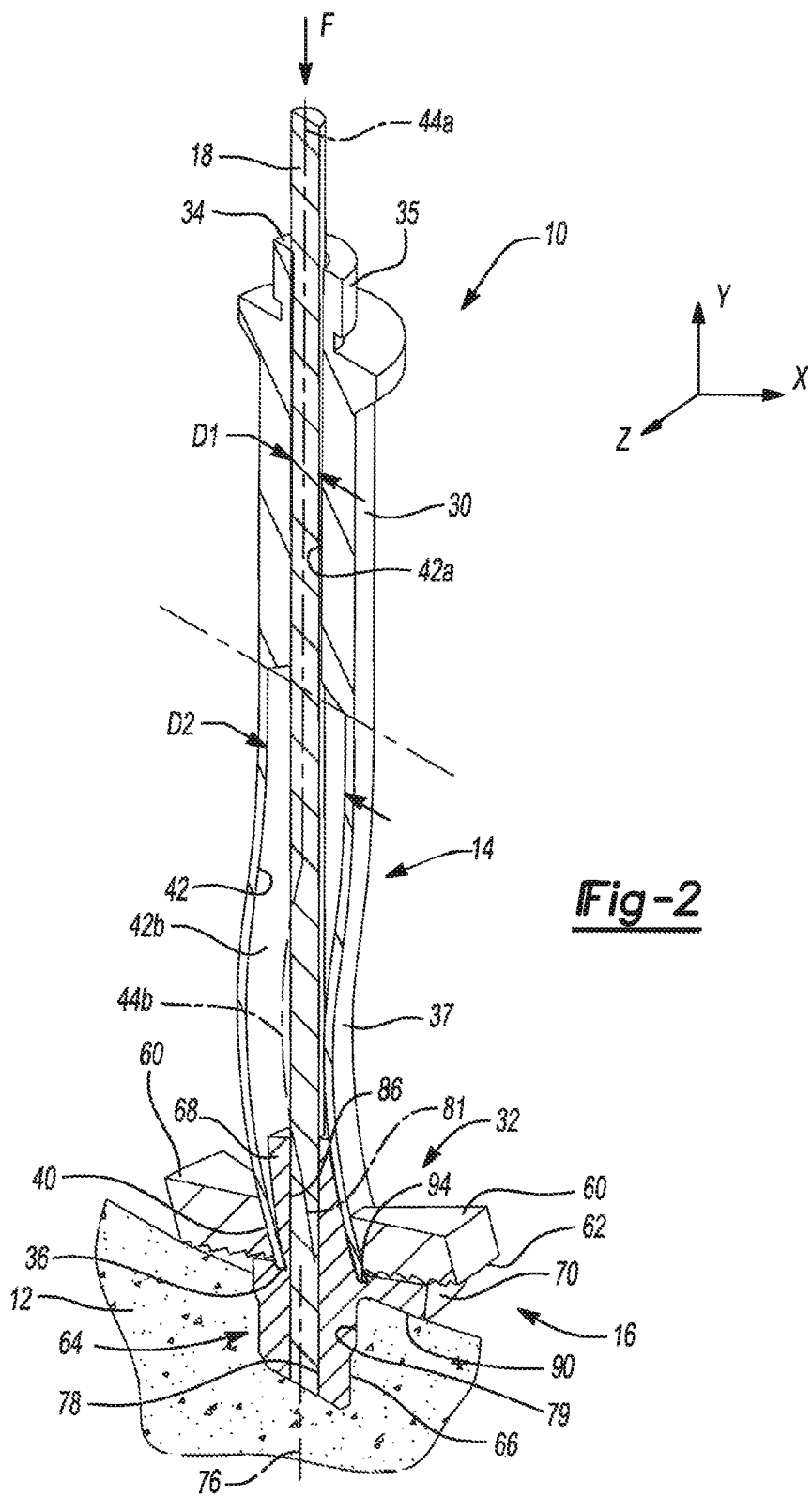
FIG. 2 is a cross-sectional view of the reaming system shown in FIG. 1.

With initial reference to FIGS. 1 and 2, a reaming system constructed in accordance with the principles of the present disclosure is illustrated and identified at reference character 10. As illustrated in FIG. 2, according to one exemplary use, the reaming system 10 may be used to prepare a glenoid 12 of a glenohumeral joint during shoulder arthroplasty. It will also be appreciated, however, that the present teachings may be adapted to prepare various bones and joints during a surgical procedure.

The reaming system 10 may generally include a reamer 14, a guide 16, and a guide wire 18. Prior to addressing the particular components of the reaming system 10, a brief discussion of the exemplary use environment is warranted. The glenohumeral joint is generally formed between a humerus (not shown) and a glenoid portion 12 of a scapula. Specifically, a portion (e.g., a humeral head) of the humerus fits into the glenoid 12 on the end of the scapula. As will become appreciated from the following discussion, a surgeon may prepare an incision that is relatively small to accommodate the reaming system 10. The reaming system 10 may subsequently be inserted through the incision to ream the glenoid 12. Subsequent to reaming, the reaming system 10 can be removed from the patient through the incision.

The reamer 14 may include a shaft 30 and a cutting element or portion 32. The shaft 30 may extend between a proximal end 34 and a distal end 36. The shaft 30 may include a driving portion 35 and a flexible portion 37. The driving portion 35 may be located at the proximal end 34, and may be conventionally configured to interface and interconnect with a drill (not shown) or other driver for rotating the reamer 14. As illustrated in FIG. 2, the shaft 30 may define a substantially hollow construct having a cannula or passage 42, including a first or upper portion 42a, and a second or lower portion 42b. The upper portion 42a may extend along a first axis 44a and include a first diameter D1. The lower portion 42b may extend along a second axis 44b and include a second diameter D2 that is greater than the first diameter D1. In one configuration, the second diameter D2 may be between one hundred and four hundred percent of the first diameter D1.

In a first position, the first and second axes 44a, 44b may extend in a direction substantially parallel to the y-axis (FIG. 1). In a second position, the flexible portion 37 may bend or otherwise flex, such that the second axis 44b may extend in more than one direction, including portions extending in directions parallel to the x-, y-, and/or z-axes (FIG. 2). The configuration of the first and second diameters D1, D2 of the passage 42 may allow the guide wire 18 to extend in a substantially linear direction (e.g., parallel to the y-axis and the first axis 44b) within the passage 42, while the flexible portion 37 of the shaft 30 flexes or otherwise extends in more than one direction, as illustrated in FIG. 2.

Figure 3:
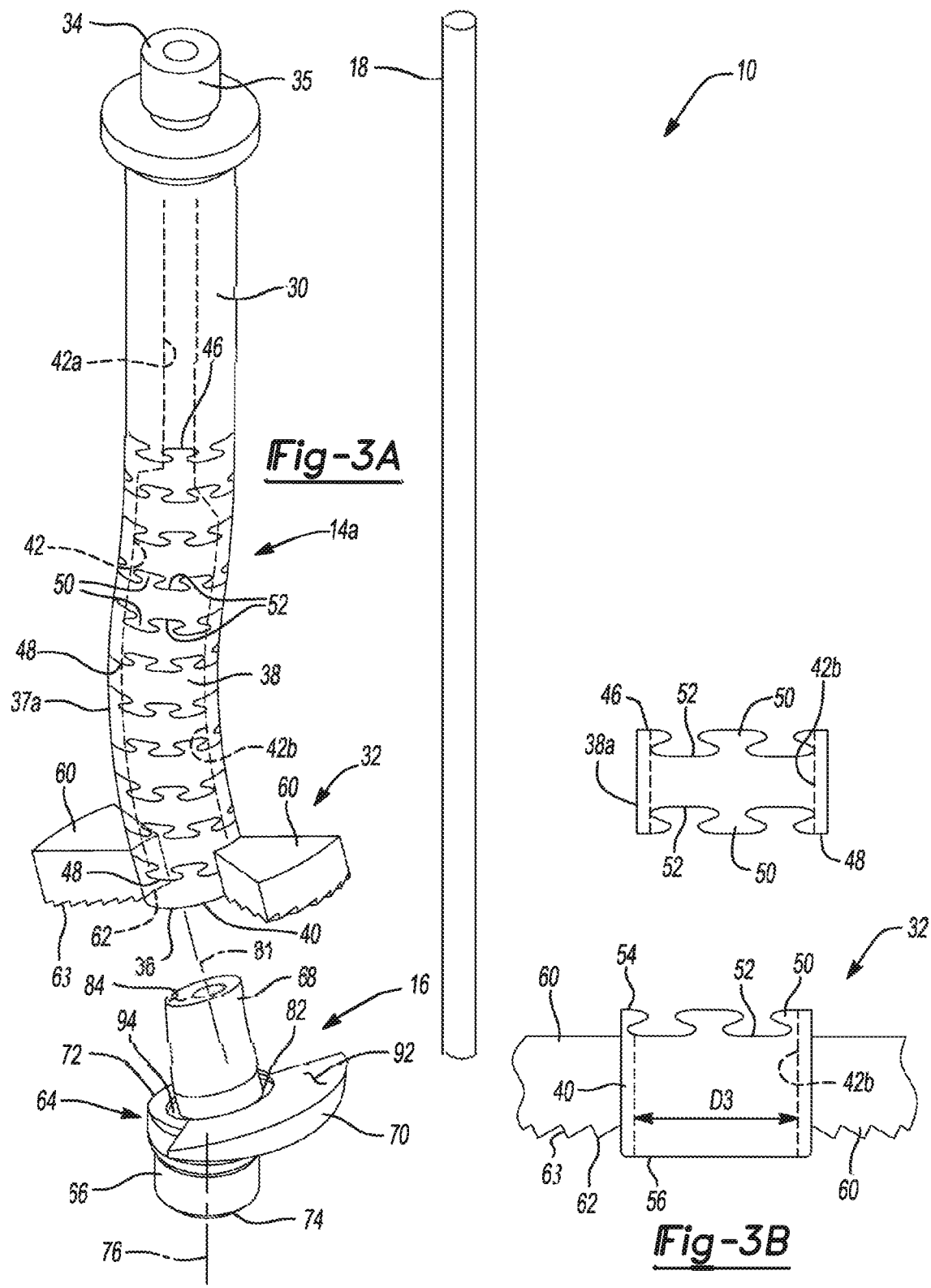
FIG. 3A is an exploded view of another reaming system constructed in accordance with the principles of the present disclosure.
FIG. 3B is an exploded view of a portion of the reaming system shown in FIG. 3A.

As illustrated in FIG. 3A, another configuration of a reaming system 10a may include a reamer 14a having a flexible portion 37a. The flexible portion 37a may include a plurality of link members 38 and a terminal ring member 40. The link members 38 and the ring member 40 may each include a substantially hollow construct, defining a lower portion 42b of the passage 42. The link members 38 may each extend between a proximal end 46 and a distal end 48. The proximal and distal ends 46, 48 may each include a plurality of axially extending lobes 50. As illustrated in FIG. 3B, in one configuration, the lobes 50 are substantially T-shaped, such that consecutive lobes 50 define a substantially T-shaped space or void 52 therebetween. In this regard, the lobes 50 and the voids 52 may be generally equally sized and spaced, such that the lobe 50 of a first link member 38 is coupled to, and hingedly engaged with, the void 52 of a second link member 38. While the lobes 50 and voids 52 are shown and described herein as being substantially T-shaped, it will be appreciated that the lobes 50 and voids 52 may have other shapes and configurations, such that the lobes 50 and voids 52 on consecutive or adjacent link members 38 are hingedly coupled to one another.

With continued reference to FIGS. 3A and 3B, the ring member 40 may extend between a proximal end 54 and a distal end 56. The proximal end 54 may include a plurality of the lobes 50 and the voids 52, such that the proximal end 54 can be coupled to, and hingedly engaged with, the distal end 48 of the link member 38. The distal end 56 of the ring member 40 may be substantially circular, defining an inner diameter D3. The inner diameter D3 may be substantially equal to the second diameter D2 of the passage 42.

The cutting portion 32 may include at least one radially extending cutting arm 60. As illustrated, in one configuration, the cutting portion 32 can include two cutting arms 60, such that the cutting portion 32 can generally provide a profile similar to a blade or propeller having a reduced overall profile that can be suitable for insertion through the incision. It will be appreciated, however, that the cutting portion 32 may include more or less than two cutting arms 60 within the scope of the present disclosure.

The cutting arms 60 may be coupled to the flexible portion 37 of the shaft 30, such that the distal end 36 of the shaft 30 may be offset from, or otherwise extend axially beyond, the cutting arms 60. With reference to FIG. 2, in one configuration the cutting arms 60 may be coupled to the ring member 40 between the proximal and distal ends 54, 56 thereof. In this regard, the distal end 56 of the ring member 40 may be offset from, or otherwise extend axially beyond, a cutting surface or distal end 62 of the cutting arms 60. The cutting arms 60 may be coupled to and supported by the ring member 40 with mechanical fasteners, a weld, or any other suitable fastening technique. In one configuration, the cutting arms 60 may be integrally and monolithically formed with the flexible portion 37 of the shaft 30. The distal end 62 of the cutting arms 60 may include a cutting surface having a plurality of cutting teeth 63 formed thereon. The cutting surfaces of each of the cutting arms 60 may collectively define a cutting plane or be disposed along a common cutting plane. The cutting plane may be axially spaced from the distal end 36 of the shaft 30.

Figure 4:
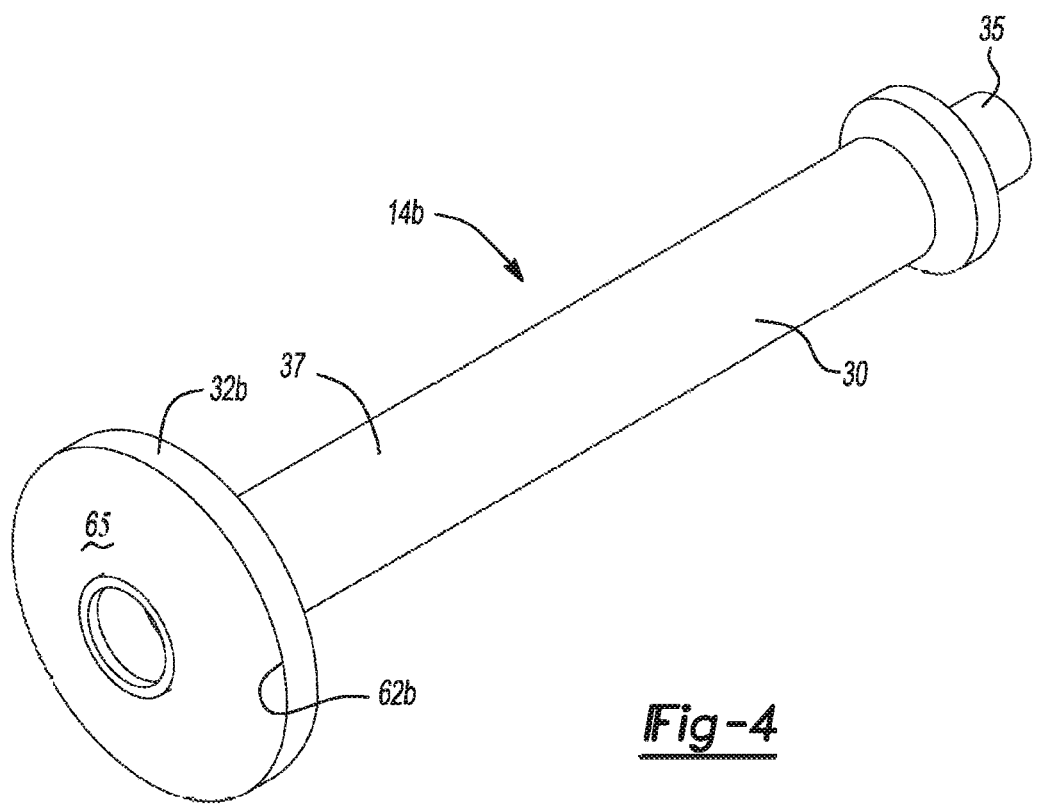
FIG. 4 is a perspective view of a reamer, for use with the reaming systems shown in FIGS. 1 and 3, constructed in accordance with the principles of the present disclosure.

With reference to FIG. 4, another configuration of a reamer 14b is shown. The reamer 14b may be used with the reaming systems 10 and 10a. In this regard, the structure and function of the reamer 14b may be similar or identical to the structure and function of the reamer 14 described above, apart from any exceptions described below and/or shown in the figures. Accordingly, similar features will not be described again in detail. Like reference numerals are used hereinafter and in the drawings to identify like components, while like reference numerals containing letter extensions (i.e., "b") are used to identify those components that have been modified.

The reamer 14b may include the shaft 30 and a cutting portion 32b. The cutting portion 32b may include a substantially circular shape. A distal end 62b of the cutting portion 32b may include a substantially spherical cutting surface 65 (shown in simplified form).

With reference to FIGS. 1, 3A and 5A, the guide 16 may include a body 64 and a flange 70. The body 64 may include a boss 66 and a hub 68. The boss 66 may extend between a proximal end 72 and a distal end 74 along a first axis 76. The distal end 74 may define a first end surface 77 extending in a direction substantially perpendicular to the first axis 76. The boss 66 may define a size and shape that corresponds to, or otherwise matches, the size and shape of an aperture 79 formed in the glenoid 12 and/or a portion of a glenoid implant (not shown). As illustrated in FIGS. 2 and 5A, the boss 66 may further define a first aperture or passage 78 extending in a direction substantially parallel to the first axis 76. In this regard, the first passage 78 may be concentrically formed relative to the boss 66.

The hub 68 may include a substantially cylindrical portion extending between a proximal end 80 and a distal end 82 along a second axis 81. The hub 68 may further define an outer diameter D4 that is substantially equal to or slightly less than the inner diameter D3 of the ring member 40. In this regard, an outer surface of the hub 68 may be tapered such that the diameter D4 may vary between the proximal and distal ends 80, 82. As illustrated in FIG. 3A, the proximal end 80 of the hub 68 may define a second end surface 84 extending in a direction substantially perpendicular to the second axis 81. With reference to FIG. 5A, the second axis 81 may define an angle $\alpha$ with the first axis 76. The angle $\alpha$ may be between five degrees (5°) and thirty degrees (30°). In one configuration, the angle $\alpha$ may be substantially equal to fifteen degrees (15°). The distal end 82 may be coupled to, or monolithically formed with, the proximal end 72 of the boss 66. In this regard, the hub 68 may extend from the boss 66 at the angle $\alpha$. The hub 68 may define a second aperture or passage 86 extending in a direction substantially parallel to the first axis 76. In this regard, as illustrated in FIGS. 1 and 5A, the second passage 86 may be eccentrically formed relative to the hub 68. In one configuration, the second passage 86 may be in communication with the first passage 78. In this regard, as illustrated in FIGS. 5A and 7, the first and second passages 78, 86 may be defined by a continuous, cylindrical inner surface 88 of the guide 16.

Figure 6:
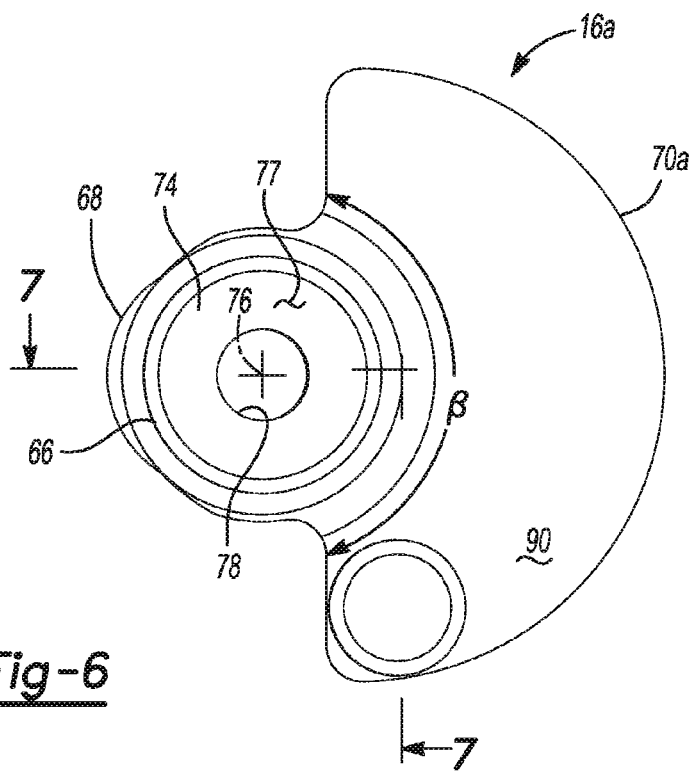
FIG. 6 is a bottom view of the guide of FIG. 5B.

With reference to FIG. 1, the flange 70 may extend radially outward from the body 64 and about the first axis 76 by an angle $\beta$. The angle $\beta$ may be between forty-five degrees (45°) and two hundred forty degrees (240°). As illustrated in FIG. 6, in one configuration, the angle $\beta$ may be substantially equal to one hundred eighty degrees (180°). In one configuration, the flange 70 may be monolithically formed with the body 64. It will be appreciated, however, that the flange 70 may also be separately formed and thereafter coupled to the body 64.

The flange 70 may include a support surface 90 (FIG. 5A) and a guide surface 92 (FIG. 1). The support surface 90 may generally face the distal end 74 of the boss 66 and extend from the body 64 in a direction substantially perpendicular to the first axis 76. In this regard, as illustrated in FIG. 5A, the support surface 90 may include a convex or spherically shaped contour to match, or otherwise align with, a portion of the glenoid 12.

Figure 7:
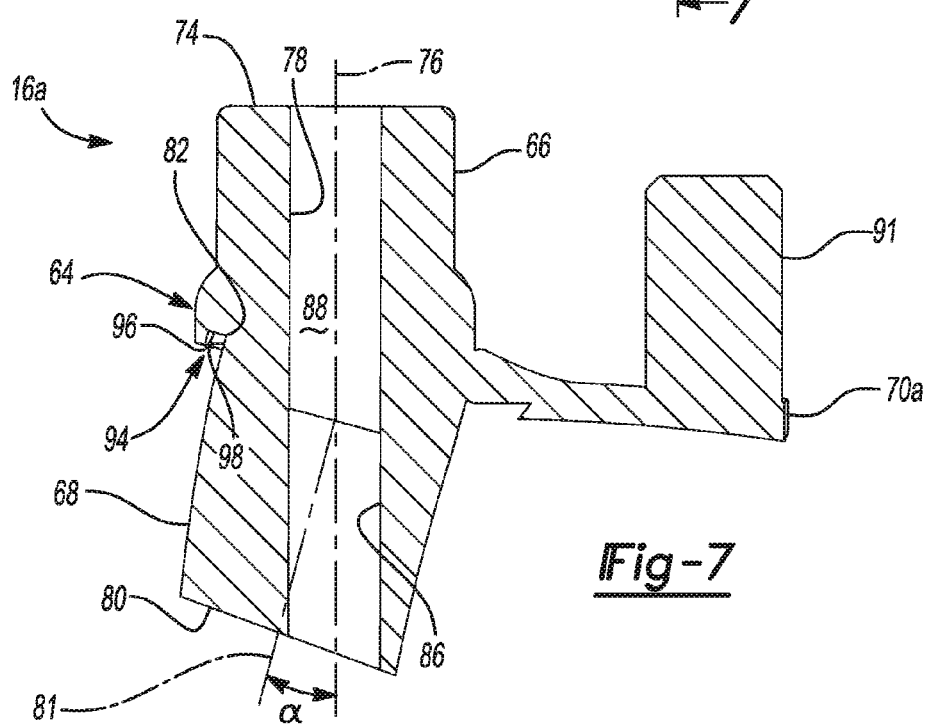
FIG. 7 is a cross-sectional view of the guide shown in FIG. 6, taken through the line 7-7.

With reference to FIGS. 5B, 6, and 7, another configuration of a guide 16a is shown. The guide 16a may be substantially similar to the guide 16, except as otherwise provided herein. Accordingly, like reference numerals may be used to describe similar features and components, and similar features and components will not be described again in detail. The guide 16a may include at least one peg portion 91 extending from the support surface 90. The peg portion 91 may include a substantially cylindrical construct extending in a direction substantially parallel to the first axis 76. In this regard, it will be appreciated that the guide 16 may be used in a reverse shoulder arthroplasty procedure, while the guide 16a may be used in an anatomic shoulder arthroplasty procedure.

With reference to FIG. 5B, the guide surface 92 may generally oppose the support surface 90 and may include a first portion 92a and a second portion 92b. The first portion 92a may extend radially outward from the body 64 in a direction substantially perpendicular to the second axis 81. The second portion 92b may extend outward from the first portion 92a in a direction substantially perpendicular to the first axis 76. In this regard, the support surface 90 and the first portion 92a of the guide surface 92 may define an angle $\delta$ therebetween. The angle $\delta$ may be substantially equal to the angle $\alpha$. Accordingly, as illustrated in at least FIGS. 5A and 5B, the flange 70, 70a may substantially define a ramp or wedge-shaped portion of the guide 16, 16a, respectively.

The guide surface 92 and the hub 68 may define a groove or channel 94 therebetween. The channel 94 may extend circumferentially about the first axis 76 and extend axially in a direction substantially parallel to the second axis 81. As illustrated in FIG. 7, the channel 94 may include a radially extending stop surface 96 and an axially extending guide surface 98 (relative to the second axis 81). In this regard, the stop surface 96 may extend in a direction substantially perpendicular to the second axis 81, and the guide surface 98 may extend in a direction substantially parallel to the second axis 81.

An example method of preparing a bone, such as the glenoid 12 for an anatomic or reverse shoulder arthroplasty procedure will now be described. First, a surgeon may prepare the incision to accommodate the reaming system 10. The guide wire 18 can be inserted through the incision and anchored into the scapula. The scapula of the glenoid 12 can be reamed or otherwise drilled to accommodate the boss 66 and/or the peg portions 91. The guide 16 can be coupled to the guide wire 18 by feeding the guide wire 18 through the first and second passages 78, 86 until the support surface 90 is adjacent to, and supported by, the glenoid 12, as illustrated in FIG. 2. In this regard, it will be appreciated that the boss 66 and the peg portion 91 may be received within bores or apertures formed in the glenoid 12.

The reamer 14 may be coupled to the guide 16 by feeding the guide wire 18 through the passage 42 until the cutting portion 32 is adjacent to the hub 68 of the guide 16. As the guide wire 18 is fed through the passage 42, the cutting portion 32 may be in a first position such that the cutting arms 60 extend in a direction substantially perpendicular to the first axis 76 (FIG. 1). As the hub 68 is received by the passage 42, the hub 68 may cause the flexible portion 37 to bend or flex, thus urging the cutting portion 32 into a second position such that the cutting arms 60 extend in a direction substantially perpendicular to the second axis 81 (FIG. 2). In this regard, it will be appreciated that the link members 38 may pivot or hinge relative to one another and relative to the ring member 40, such that the cutting portion 32 is moved from the first position to the second position. In both the first and second positions, the guide wire 18 may extend in a direction substantially parallel to the first axis 44a of the reamer 14 and substantially parallel to the first axis 76 of the guide 16, as illustrated in FIG. 2. In the second position, the cutting arms 60 can contact the glenoid 12.

The driving portion 35 of the reamer 14 can be coupled to the drill, or other similar driving device, that can be used to rotate the reamer 14 about the guide wire 18. As the reamer 14 is rotated, the surgeon may apply a force F at the proximal end 34 of the shaft 30 in a direction substantially parallel to the first axis 76 (FIG. 2) The force F may include a first component extending in a direction substantially perpendicular to the second axis 81, and a second component extending in a direction substantially parallel to the second axis 81. As the reamer 14 rotates, the cutting arms 60 can ream or otherwise remove a portion of the glenoid 12 until the distal end 36 of the shaft 30 is received within the channel 94 and abuts the body 64, as illustrated in FIG. 2. In this regard, it will be appreciated that the shaft 30 and the guide surface 98 of the channel 94 can help to stabilize the reamer 14 and the stop surface 96 of the channel 94 can help to control the depth of the cut provided in the glenoid 12, thus ensuring that the cutting arms 60 do not contact or otherwise interfere with the flange 70 during the reaming operation.

It will be appreciated that the reaming system 10, including the shaft 30 having the flexible portion 37, and the guide 16 having the boss 66 extending along the first axis 76 and the hub 68 extending along the second axis 81, provides a number of advantages, including allowing the surgeon to correct bone deformities (e.g., glenoid erosion) in a way that minimizes excessive reaming of the glenoid 12. By minimizing excessive reaming of the glenoid 12, the system 10 can help to save valuable time during the surgical procedure, while also helping to ensure a consistent reaming process, and thus consistent results in the reamed glenoid 12.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A bone reaming system comprising:
a bone reamer including a shaft and a cutting element carried by the shaft, the shaft including an outer surface extending from a proximal end to a distal end of the shaft, the distal end including a distal shaft opening, the cutting element including a distally-facing cutting surface positioned adjacent to the distal end and comprising a plurality of cutting teeth extending therefrom, the cutting surface extending along a cutting plane that is substantially perpendicular to the outer surface of the shaft at the distal end; and
a guide including a flange portion supported by a body portion of the guide, the flange portion extending radially from the body portion and including a bone-contacting support surface and an opposite guide surface, the body portion including a boss extending away from the support surface along a first longitudinal axis and configured for insertion within a bone, a hub extending away from the guide surface along a second longitudinal axis and configured to be at least partially received within the distal shaft opening such that the cutting element is rotatable about the second longitudinal axis, and a cannula formed within the boss and the hub and extending along the first longitudinal axis, the second longitudinal axis forming an acute angle with the first longitudinal axis.

2. The bone reaming system of claim 1, wherein the guide surface extends in a direction substantially perpendicular to the second longitudinal axis.

3. The bone reaming system of claim 2, wherein the support surface defines a substantially spherical profile.

4. The bone reaming system of claim 1, wherein the hub includes a tapered cute surface.

5. The bone reaming system of claim 1, wherein the guide surface includes a channel disposed about the hub, the channel extending in a direction substantially parallel to the second longitudinal axis.

6. The bone reaming system of claim 5, wherein the channel includes a stop surface extending in a direction substantially perpendicular to the second longitudinal axis.

7. The bone reamer of claim 1, wherein the shaft defines a cannula.

8. The bone reamer of claim 7, wherein the cannula includes a first portion having a first diameter and a second portion having a second diameter greater than the first diameter.

9. The bone reamer of claim 8, wherein the shaft includes a flexible onion disposed between the proximal and distal ends, and wherein at least a portion of the second portion is aligned with the flexible portion of the shaft.

10. The bone reamer of claim 1, wherein the cutting element is monolithically formed with the shaft.

11. The bone reamer of claim 1, wherein the cutting surface is offset proximally from the distal end of the shaft.

12. A bone reaming system comprising:
a bone reamer including a shaft and a cutting element affixed to and rotatable with the shaft, the shaft including a proximal end and a distal end, the cutting element being offset proximally from the distal end, and the distal end including a distal shaft opening; and
a guide including a flange portion supported by a body portion of the guide, the flange portion extending radially from the body portion and including a bone-contacting support surface and an opposite guide surface, the body portion including a boss extending away from the support surface along a first longitudinal axis and configured for insertion within a bone, a hub extending away from the guide surface along a second longitudinal axis and configured to be at least partially received within the distal shaft opening such that the cutting element is rotatable about the second longitudinal axis, and a cannula formed within the boss and the hub and extending along the first longitudinal axis, the second longitudinal axis forming an acute angle with the first longitudinal axis, wherein the guide surface includes a channel disposed about the hub, the channel extending in a direction substantially parallel to the second longitudinal axis and configured to receive the distal end of the shaft when the hub is at least partially received within the distal shaft opening.

13. The bone reaming system of claim 12, wherein the shaft of the bone reamer is cannulated.

14. The bone reaming system of claim 13, wherein the cutting element includes a plurality of radially extending cutting arms.

15. The bone reaming system of claim 12, wherein the guide surface extends in a direction substantially perpendicular to the second longitudinal axis.

16. The bone reaming system of claim 15, wherein the support surface defines a substantially spherical profile.

17. A bone reaming system comprising:
a bone reamer including a shaft and a cutting element affixed to and rotatable with the shaft, the shaft including a proximal end and a distal end, the cutting element being offset proximally from the distal end, and the distal end including a distal shaft opening; and
a guide including a flange portion supported by a body portion of the guide, the flange portion extending radially from the body portion and including a bone-contacting support surface and an opposite guide surface, the body portion including a boss extending away from the support surface along a first longitudinal axis and configured for insertion within a bone, a hub extending away from the guide surface along a second longitudinal axis and configured to be at least partially received within the distal shaft opening such that the cutting element is rotatable about the second longitudinal axis, a channel defined in the guide surface about the hub extending in a direction substantially parallel to the second longitudinal axis, and a cannula formed within the boss and the hub and extending along the first longitudinal axis, the second longitudinal axis forming an acute angle with the first longitudinal axis;
wherein the distal end of the shaft is configured to be received within the channel to control a cutting depth of the cutting element.

* * * * *

UNITED STATES PATENT AND TRADEMARK OFFICE
CERTIFICATE OF CORRECTION

| | | |
|---|---|---|
| PATENT NO. | : 11,311,301 B2 | Page 1 of 1 |
| APPLICATION NO. | : 16/749684 | |
| DATED | : April 26, 2022 | |
| INVENTOR(S) | : Kovacs et al. | |

It is certified that error appears in the above-identified patent and that said Letters Patent is hereby corrected as shown below:

On the Title Page

On page 2, in Column 2, item (56) under "Foreign Patent Documents", Line 2, delete "198461" and insert --1984610 A-- therefor On page 3, in Column 1, item (56) under "Other Publications", Line 31, delete "Nov. 2, 2018"," and insert --Nov. 20, 2018",-- therefor In the Claims In Column 9, Line 2, in Claim 4, delete "cute" and insert --outer-- therefor In Column 9, Line 10, in Claim 7, delete "reamer" and insert --reaming system-- therefor In Column 9, Line 12, in Claim 8, delete "reamer" and insert --reaming system-- therefor In Column 9, Line 16, in Claim 9, delete "reamer" and insert --reaming system-- therefor In Column 9, Line 17, in Claim 9, delete "onion" and insert --portion-- therefor In Column 9, Line 20, in Claim 10, delete "reamer" and insert --reaming system-- therefor In Column 9, Line 22, in Claim 11, delete "reamer" and insert --reaming system-- therefor Signed and Sealed this
Twenty-eighth Day of June, 2022

Katherine Kelly Vidal
*Director of the United States Patent and Trademark Office*